United States Patent [19]

Bawa

[11] Patent Number: 4,668,506

[45] Date of Patent: May 26, 1987

[54] SUSTAINED-RELEASE FORMULATION CONTAINING AND AMINO ACID POLYMER

[75] Inventor: Rajan Bawa, Fairport, N.Y.

[73] Assignee: Bausch & Lomb Incorporated, Rochester, N.Y.

[21] Appl. No.: 766,741

[22] Filed: Aug. 16, 1985

[51] Int. Cl.$^4$ .................. A61K 31/74; G03B 21/46; C08F 226/10; B29D 11/00

[52] U.S. Cl. ............................ 424/429; 424/486; 604/893; 604/894; 604/895; 351/160 R; 351/160 H; 351/177; 523/106; 523/107; 523/108; 514/912; 514/913; 514/954

[58] Field of Search .............. 424/19, 21; 604/893, 604/894, 895; 351/160 R, 160 H, 177; 523/106, 107, 108; 514/912, 913, 954

[56] References Cited

U.S. PATENT DOCUMENTS

| | | | |
|---|---|---|---|
| 3,220,960 | 11/1965 | Wichterle et al. | 521/149 |
| 3,496,254 | 2/1970 | Wichterle | 523/106 |
| 3,551,556 | 12/1970 | Kliment et al. | 424/21 |
| 3,557,261 | 1/1971 | Wichterle | 523/106 |
| 3,641,237 | 2/1972 | Gould et al. | 424/16 |
| 3,786,812 | 1/1974 | Neefe | 351/177 |
| 3,811,444 | 5/1974 | Heller et al. | 604/894 |
| 3,812,071 | 5/1974 | Stoy et al. | 523/106 |
| 3,822,089 | 7/1974 | Wichterle | 526/216 |
| 3,826,258 | 7/1974 | Abraham | 424/19 |
| 4,003,991 | 1/1977 | Krohn et al. | 424/78 |
| 4,143,949 | 3/1979 | Chen | 351/160 H |
| 4,152,508 | 5/1979 | Ellis et al. | 526/279 |
| 4,153,641 | 5/1979 | Deichert et al. | 526/270 |
| 4,158,089 | 6/1979 | Loshaek et al. | 351/160 H |
| 4,182,802 | 1/1980 | Loshaek et al. | 351/160 H |
| 4,184,992 | 1/1980 | Hosaka | 351/160 H |
| 4,271,143 | 6/1981 | Schoenwald et al. | 424/78 |
| 4,279,795 | 7/1981 | Yamashita et al. | 351/160 H |
| 4,361,689 | 11/1982 | Patel et al. | 523/108 |
| 4,436,887 | 3/1984 | Chromecek et al. | 526/259 |
| 4,440,919 | 4/1984 | Chromecek et al. | 526/259 |
| 4,462,665 | 7/1984 | Shah | 351/160 H |
| 4,483,846 | 11/1984 | Koide et al. | 424/19 |
| 4,534,916 | 8/1985 | Wichterle | 523/106 |
| 4,536,554 | 8/1985 | Lim et al. | 523/108 |
| 4,563,490 | 1/1986 | Stol et al. | 523/106 |

*Primary Examiner*—Ronald W. Griffin
*Attorney, Agent, or Firm*—Bernard D. Bogdon; DeWitt M. Morgan

[57] ABSTRACT

A sustained-release polymeric hydrogel dosage form useful for topical, systemic or transdermal administration of a medicinal agent comprising a cross-linked, polymerized hydrophilic polymer, an amino acid polymer, a cross-linking agent, an optional hydrophobic polymer and said medicinal agent in a therapeutically effective amount.

27 Claims, 13 Drawing Figures

Fig. 1

RELEASE CHARACTERISTICS OF A HIGH WATER SPIN POLYMERIC HYDROGEL WITH PILOCARPINE HYDROCHLORIDE IN DISTILLED WATER

Fig. 2

RELEASE CHARACTERISTICS OF OCUSERT-20® IN DISTILLED WATER

Fig. 3

RELEASE CHARACTERISTICS OF
OCUSERT-40® IN DISTILLED WATER

Fig. 4

RELEASE CHARACTERISTICS OF
PERMALENS® WITH PILOCARPINE
HYDROCHLORIDE IN DISTILLED WATER

Fig. 5.

RELEASE CHARACTERISTICS OF A HIGH WATER SPIN POLYMERIC HYDROGEL WITH PILOCARPINE HYDROCHLORIDE IN DISTILLED WATER

Fig. 6

RELEASE CHARACTERISTICS OF A HIGH WATER SPIN POLYMERIC HYDROGEL WITH PILOCARPINE HYDROCHLORIDE IN BUFFERED SALINE

Fig. 8

SUSTAINED-RELEASE FORMULATION CONTAINING AND AMINO ACID POLYMER

BACKGROUND OF THE INVENTION

1. Field of the Invention

This invention relates generally to a novel sustained-release formulation which gradually releases a medicinal agent therefrom. More specifically, the invention pertains to the use of the formulation for slowly dispensing a drug in the eye.

2. Description of Related Art

It is basically known in the art that medicinally active substances may be dissolved in the aqueous constituent of hydrogels to gradually release such substances over an extended period. For example, U.S. Pat. No. 3,220,960 describes utilizing a hydrogel in the eye as a carrier for time release medicaments such as boric acid or penicillin. Similarly, U.S. Pat. Nos. 3,551,556; 3,641,237; 4,003,991; and 4,271,143 disclose slowly releasing an active ingredient from an insoluble, cross-linked hydrogel in one form or another. Several compositions illustrated in the latter two patents are comprised of viscous, long-acting gel preparations where the prolongation of biological activity of the ophthalmic drug results from a slow erosion of the gel surface. The formulation in U.S. Pat. No. 3,551,556 shows granular non-ionogenic, neutral, insoluble hydrogels which are useful for oral or intramuscular application. Further, many patents are directed to ocular insert devices which prolong the effect of a drug incorporated within the device. Such patents include U.S. Pat. Nos. 3,811,444; 3,826,258; and 3,786,812.

The prior carriers of medicaments present certain difficulties during their use, particularly with ophthalmic drugs. The predominant complaint with long-acting gel formulations is blurred vision. Another difficulty is the inability to wear corrective contact lenses when a viscous material will be instilled and remain in the eye over an extended period of time. The ocular insert devices also present certain disadvantages with their use. When inserted into the conjuctival sac, such devices create a strong foreign body sensation and discomfort for the patient. The insert devices must be changed weekly. Additionally, the devices tend to fall out of the eye easily and cannot be used further by the patient since they are not capable of being sterilized.

Similarly, conventional contact lenses containing a sustained-release medicine carrier have drawbacks in practice. They have been found to obtain inadequately controlled or prolonged release characteristics making the conventional lenses unsuitable and impractical as sustained-release devices. The concept of soaking a high water content material in a drug solution has been used with conventional hydroxyethyl methacrylate based contact lenses, for example, a polymerized hydrophilic monomer or soft contact lens such as Soflens ® manufactured Bausch & Lomb. See Ruben et al.; British J. Ophthal., 59: 455 (1975). In practice, Soflens ®, however, provides an inefficient system and is an unsuitable device for prolonged release. Experimental studies have shown that Soflens ® will release 100% of pilocarpine hydrochloride in buffered saline and distilled water in merely 1½ and 2½ hours, respectively.

SUMMARY OF THE INVENTION

It is therefore an important object of the present invention to provide a highly unique sustained-release polymeric hydrogel dosage form which does not undergo decomposition or deterioration in body fluids and is nontoxic therein.

Another object is to provide a sustained-release polymeric hydrogel dosage form that is useful for topical, systemic or transdermal administration of medicinal agents, particularly ophthalmic drugs.

A further object is to provide a polymeric matrix which is moldable to any desired shape, with moldability to the shape of the cornea of the eye being of major interest.

A still further object is to provide a sustained-release dosage form for ophthalmic administration which does not affect eyesight and is well-tolerated and pleasing to the patient.

Another further object is to provide an ophthalmic dosage form that can concurrently correct vision and release medication to the eye, i.e., a contact lens with both cosmetic and therapeutic value.

Further purposes and objects of the present invention will appear as the specification proceeds.

With the foregoing and other objects in view, the invention herein provides a sustained-release polymeric hydrogel dosage form useful for topical, systemic or transdermal administration of a medicinal agent comprising cross-linked polymerized hydrophilic polymers, an amino acid polymer, a cross-linking agent and optionally one or more hydrophobic polymers. The background of the invention and its departure from the art will be further described hereinbelow with reference to the accompanying drawings, wherein:

DESCRIPTION OF THE PREFERRED EMBODIMENTS

In accordance with the present invention, the formulation employed as a sustained-release dosage form includes one or more hydrophilic polymers having an olefinic bond, an alpha-, beta-unsaturated carbonyl modified or unmodified amino acid polymer, a cross-linking agent and optionally one or more hydrophobic polymers. The formulation contains a medicinal agent for the controlled-release administration to mammals of the desired active ingredient from the polymeric matrices.

The hydrophilic monomer used in the polymer of this invention can be present in varying amounts, desirably about 50% to about 90% w/w and, more preferably, about 83% to about 84% w/w of the total monomers present in the polymerization mixture. These monomers have an olefinic bond. They include, for example, the hydroxyalkyl esters and amides, both N-substituted and unsubstituted, of alpha-, beta-unsaturated carboxylic acid, N-vinyl lactams and 2-acrylamido-2-methylpropane sulfonic acid. The alpha-, beta-unsaturated acids useful in this invention are acrylic acid, crotonic acid, methacrylic acid, itaconic acid, maleic acid, maleic anhydride, fumaric acid and the like. The poly-functional alcohols which form the hydroxyalkyl esters include glycol, glycerol, propylene glycol, trimethylene glycol and other polyhydric alkanols, dialkylene glycols of 2 to 12 carbon atoms, polyalkylene glycols, etc. Polyalkylene glycols are exemplified by triethylene glycol, tetraethylene glycol, pentaethylene glycol, hexaethylene glycol and the like. The preferred hydrophilic monomers are the hydroxyalkyl esters, specifically hydroxyethyl methacrylate (HEMA).

Useful amides of the foregoing acids include diacetone acrylamide and N-mono-substituted diacetone acrylamide. Also useful are the amines of the foregoing acids such as mono- or di-alkylamino substituents.

A nitrogen containing monomer which may be used in the preparation of the polymers and copolymers of this invention is conveniently referred to as N-vinyl lactam which includes (a) N-vinyl-lactams per se and (b) other heterocyclic N-vinyl monomers. Illustrative of the N-vinyl lactams that are employed in this invention are N-vinyl-2-pyrrolidinone, N-(1-methyl vinyl)pyrrolidinone, N-vinyl-2-piperidone, N-vinyl-2-caprolactam and the like which may be substituted in the lactam ring by one or more lower alkyl groups such as methyl, ethyl or propyl, e.g., N-vinyl-5-methyl pyrrolidinone, N-vinyl-3,3-dimethyl pyrrolidinone, N-vinyl-5-ethyl pyrrolidinone, N-vinyl-6-methyl piperidone, etc. Illustrative of the other heterocyclic N-vinyl monomers used in preparing the polymers of this invention are N-vinyl imidazole, N-vinyl succinimide, N-vinyl diglycolylimide, N-vinyl glutarimide, N-vinyl-3-morpholinone, N-vinyl-5-methyl-3-morpholinone, etc. The lactams may be effectively employed alone or in admixture with other lactam monomers to give hydrogels having the foregoing desirable characteristics.

The second monomeric component of the polymer of this invention is an alpha-, beta-unsaturated carbonyl modified or unmodified amino acid monomer or monomers. This component can be present in varying amounts, desirably in an amount from about 5% to about 27% w/w and, more preferably, about 6% w/w of the total monomers present in the polymerization mixture. The modified or unmodified amino acid monomers are hydrophilic compounds which contribute significantly to the swelling of the polymer in water and permit higher oxygen diffusion.

The alpha-, beta-unsaturated carbonyl modifier for the modified amino acids of this invention may be, for example, acrylic acid, crotonic acid, methacrylic acid, maleic acid, fumaric acid, itaconic acid and their functional derivatives, i.e., acid chlorides, anhydrides, amides and esters. The more preferred modifiers are methacrylic acid and methacroyl chloride.

An amino acid is an organic acid whose molecule contains both a carboxyl group (COOH) and an amino group ($NH_2$) coupled with an alkyl, cycloalkyl, aryl or heterocyclic structure, the alkyl, cycloalkyl or heterocyclic structure being free of olefinic unsaturation. The alpha-, beta-carbonyl substituent can be attached to either the amino group or the hydroxy group of the amino acid, depending on the structure of the amino acid. Additionally, the carbonyl substituent can attach to other reactive groups, if present, in the amino acid, e.g., thiol (SH) or phenolic hydroxyl.

Amino acids useful in the preparation of the modified acids of this invention include, but are not limited to, beta-alanine, gamma-aminobutyric acid, omega-aminocaproic acid, omega-aminododecanoic acid, beta-cycanoalanine, epsilon-methylhistidine, canavanine, djenkolic acid, 1-azaserine, gamma-methylene glutamic acid, N-methyltyrosine, glycine, alanine, serine, cystine, cysteine, lanthionine, phenylalanine, tyrosine, diiodotyrosine, tryptophan, histidine, aminobutyric acid, methionine, valine, norvaline, leucine, isoleucine, norleucine, arginine, ornithine, lysine, aspartic acid, glutamic acid, threonine, hydroxyglutamic acid, proline, hydroxyproline, asparagine, glutamine, desmosine, isodesmosine, 5-hydroxylysine and the like. Preferred amino acids are glycine, glutamic acid, desmosine and isodesmosine.

It should be understood that other, though perhaps less common, amino acids occurring in nature or prepared synthetically, including those shown in the examples which follow, are within the scope of this invention. Reactive sites on the amino acids can be partially blocked by saturated nonpolymerizable substituents provided that one reactive site is substituted by the alpha-, beta-carbonyl substituent.

The polymers used in this invention are cross-linked by all types of cross-linking compounds used in the prior art, see for instance, U.S. Pat. Nos. 3,822,089; 4,152,508; and 4,440,919. The cross-linking agent can be employed in varying amounts and desirably in an amount from about 0.1% to about 20% w/w, preferably 0.5% w/w, of the total monomers present. Examples of cross-linking agents include polyfunctional derivatives of the previously enumerated alpha-, beta-unsaturated acids, e.g., acrylic acid, methacrylic acid, crotonic acid, itaconic acid, maleic acid, fumaric acid, acrylamide, methacrylamide, multi-vinyl substituted benzenes, etc.

More particularly these cross-linking agents include, but are not limited to, the following: ethylene glycol diacrylate or dimethacrylate, diethylene glycol diacrylate or dimethacrylate, triethylene glycol diacrylate or dimethacrylate, tetraethylene glycol diacrylate or dimethacrylate, polyethylene glycol diacrylate or dimethacrylate, trimethylolpropane triacrylate or trimethacrylate, bisphenol A diacrylate or dimethacrylate, ethoxylated bisphenol A diacrylate or dimethacrylate, pentaerythritol tri- and tetra-acrylate or methacrylate, tetramethylene diacrylate or dimethacrylate, methylene bisacrylamide or methacrylamide, dimethylene bisacrylamide or methacrylamide, N,N'-dihydroxyethylene bisacrylamide or methacrylamide, hexamethylene bisacrylamide or methacrylamide, decamethylene bisacrylamide or methacrylamide, divinyl benzene, vinyl methacrylate, allyl methacrylate, etc.

Still other useful cross-linking agents include 1,3-bis(4-methacryloyl oxyalkyl)tetra disiloxane and similar poly(organo-siloxane) monomers set forth in U.S. Pat. No. 4,153,641. Another group of useful cross-linking agents are the resonance free di(alkylene tertiary amine) cyclic compounds, e.g., N,N'-divinyl ethylene urea, as disclosed in U.S. Pat. No. 4,436,887. Yet another group are di- or polyvinyl ethers of di- or polyvalent alcohols such as ethylene glycol divinyl ether.

For some applications the polymerizates formed from the above hydrophilic monomers(s), modified or unmodified amino acid monomer(s) and cross-linking agent(s) may lack the desired physical handling properties. It is another aspect of this invention in such circumstances to incorporate one or more hydrophobic monomers in the above polymers in varying amounts, desirably from about 8% to about 20% w/w of the total monomers present. More preferably the hydrophobic monomer would be present in an amount of about 10% w/w of the total monomers present. Among other things, the hydrophobic monomers are useful as modulus modifiers.

The modulus modifier may be, for example, cycloalkyl ester, tertiary-butyl styrene, polycyclic acrylate or methacrylate, and the like as well as mixtures thereof. More particularly the polycyclic modifiers may be isobornyl acrylate, isobornyl methacrylate, dicyclopentanedienyl acrylate, dicyclopentanedienyl methacrylate, adamantyl acrylate, adamantyl methacrylate, isopinocamphyl acrylate, isopinocamphyl methacrylate, etc. and mixtures thereof. The cycloalkyl ester modifier is of formula I below. Illustrative of these cycloalkyl modifiers are menthyl methacrylate, menthyl acrylate, tertiary-butyl cyclohexyl methacrylate, isohexyl cyclopentyl acrylate, methylisopentyl cyclooctyl acrylate and the like.

(I)

wherein:
D is branched or normal alkyl of 3 to 6 carbon atoms
E is H or $CH_3$
Z is H or $CH_3$
n is an integer from 3 to 8.

In addition to the modulus modifiers other well known hydrophobic monomers may be used in the formulation of the polymers and copolymers of this invention to further tailor the properties to the particular application. The hydrophobic monomers of this invention include monomers which contain at least one silicon or fluorine atom as a part of its composition. Hydrophobic monomers include alkyl, cyclo-alkyl and aryl acrylates and methacrylates as well as mono- or disubstituted itaconates, styrene and its derivatives, acrylonitrile, vinyl esters such as vinyl acetate or vinyl pentacetyl gluconate, vinyl ethers such as vinyl butyl ether, allyl esters such as allyl acetate, propionate or butyrate, fluorine containing monomers such as octafluoropentyl methacrylate and silicon containing monomer, e.g., 1,1,1-tris(trimethoxysiloxy)-3-methacryloxypropylsilane or heptamethyltrisiloxanyl ethyl acrylate.

The monomeric mixtures, comprising the hydrophilic monomer(s), the modified or unmodified amino acid monomer(s), the optional hydrophobic monomer(s) and a cross-linking agent, are generally clear, colorless liquids of varying viscosity. These monomer mixtures can be readily cured to cast shapes by conventional methods such as free radical initiation.

As catalysts for carrying out the polymerization, there may be employed a free radical catalyst (intiator) in varying amounts and typically in the range of about 0.05% to 3% w/w of the polymerizable monomer mixture. The preferred amount of catalyst is 0.1% to 0.5% w/w of the total monomers present. Usually, the catalyst is added initially to the monomers and then the polymerization procedure is completed. The free radical type initiators suitable for this invention include peroxides, azo compounds, oxidation-reduction systems and similar initiators described in the literature. Typical catalysts include benzoin methyl ether, tertiary-butyl-peroctoate, benzoyl peroxide, isopropyl percarbonate, methyl ethyl ketone peroxide, cumene hydroperoxide, dicumyl peroxide, bis(isopropyl)peroxydicarbonate, 2,2'-azobis[isobutyronitrile], acetyl peroxide, lauroyl peroxide, decanoyl peroxide, 2,2'-azobis[2,4-dimethylvaleronitrile], phthalic peroxide, diethoxyacetophenone, tertiary-butyl peroxypivalate and the like. Thermal catalysts, visible light or irradiation, e.g., by ultraviolet light or gamma rays, also can be employed to catalyze the polymerization. Polymerization can be done at 20° to 150° C., usually 40° to 90° C.

Water soluble diluents may used with the foregoing polymers to modify the physical properties of these polymers. More particularly, the diluents may be advantageous in improving machinability and swell characteristics of the polymer. Typically, the amount of diluent will be less than 50 weight percent of the total monomers employed and preferably not more than 30 weight percent. In a particular polymer system, the limiting amount of diluent is the solubility of the diluent in the monomer system. Thus, there should be no phase separation between diluent and starting monomer mixture. Additionally, excessive amounts of diluent will result in collapse of the cell structure of the finished biomedical devices when the device is hydrated, i.e., replacement of diluent by water. The maximum amount of diluent is readily ascertained by swelling the diluent free polymer in the proposed diluent and measuring the degree of swell. Comparable results are obtained when using solvent soluble diluents wherein the solvent does not affect the lens polymer. These solvents include ketones, e.g., methyl ethyl ketone and isopropyl alcohol. Suitable diluents include ethylene glycol, glycerin, liquid polyethylene glycols, butanol butanol/water mixtures, ethylene oxide/propylene oxide block copolymers having a molecular weight from 1,000 to 5,000, linear poly(vinyl pyrrolidinone) having a molecular weight from 500 to 10,000, low molecular weight linear poly(hydroxyethyl methacrylate), glycol esters of lactic acid, formamide, dimethyl formamide, methyl ethyl ketone, dimethyl sulfoxide and the like. In the finished biomedical device, it will be necessary to replace any diluent with an aqueous solution. With respect to contact lenses, the final water content of the polymeric composition typically ranges from about 30% to about 95% w/w. The contact lens should, of course, contain a physiological saline solution as the aqueous medium.

Using methods well known in the art, the sustained-released formulation of this invention can be formed into a variety of shapes depending upon the end use and desired results to be obtained therefrom. For ophthalmic purposes, the polymeric hydrogel could have any form to maintain direct contact with the eye. It is not necessary to cover the entire cornea if the dosage form is merely used to instill a continuous flow of an ophthalmic drug in the eye. If the hydrogel will also be used to correct vision, then it may be desirable to cast the polymer on an optical mold.

By way of example, the mixture of hydrophilic monomer(s), modified or unmodified amino acid monomer(s), cross-linking agent, free radical initiator and optional hydrophobic monomer(s) described above is purged with an inert gas such as nitrogen or carbon dioxide and filled into polypropylene tubes having dimensions of 18 mm × 300 nm. The polymerization is then carried out by gradually heating from 30° C. to 110° C. in a step fashion over a span of several days. In a typical schedule the tubes are placed in a water bath from 30° C. to 50° C. for two to three days followed by two days at 60° C. The rod is then removed from the mold and post-cured at 110° C. for a period of about four hours. The fully cured rods are then cut into cylinders, optionally then annealed at temperatures up to 150° C. and machined to form contact lenses as desired. A spin-casting process as described in U.S. Pat. No. 3,408,429 and 3,496,254 can be employed to prepare useful objects of this invention. The manufacturing technique may involve triple spin-casting or a casting method that does not involve spinning. Such static casting optionally may use polypropylene domes for lens shape and easy detachment from the lens surface. Of course, any conventional material which can give a proper lens shape would suffice.

This invention contemplates a variety of processes for preparing the sustained-release polymeric hydrogel dosage form whereby the medicinal agent is retained by the polymeric matrix and, upon tissue contact, is gradually released into the tissue. One process comprises incorporating the medicament directly into the monomer mixture and polymerizing the monomers in the presence of the drug to make a single homogeneous layer of polymer plus drug as the dosage form. Another process uses the drug-polymer layer as a middle layer in a "sandwich" dosage form in which two drug-free polymer layers are formed on either side of the middle layer containing the drug. Alternatively, a two layer system may be formed having one layer as polymer plus drug and the other layer as drug-free polymer. The amount of the drug used in the preparation of these dosage forms will vary depending upon the physicochemical properties of the selected drug and the therapeutic effect desired to be achieved. Typically, the drug is added on an equivalency basis, that is, an equivalent for equivalent basis of drug to the amino acid monomer. Although a stoichiometric number of equivalents of drug and the amino acid monomer is preferred, other amounts can also be used. As an example of pilocarpine hydrochloride, varying concentrations of the compound may be employed, desirably an amount from about 0.5% to about 12% w/w, and preferably 11.43% w/w, for incorporation in the dosage form of choice.

In addition to the above dosage forms, the polymeric hydrogel of the instant invention may be prepared without the medicinal agent and then soaked in an aqueous solution of a therapeutically effective amount of the medicinal agent for a sufficient amount of time for equilibration. The amount of time for equilibration will vary depending on the physiochemical nature and concentration of the particular medicament solution. For example, the soaking time may be about 12 to 24 hours, preferably 24 hours, for a particular medicament such as pilocarpine hydrochloride at varying concentrations, desirably from about 2% to about 8% w/w.

Regardless of the exact mode of preparation, the polymeric composition provides appreciable time release of the medicament. The release rate varies with cross-linking density, type of polymer barrier system and mode of preparation. For example, a homogeneous layer of polymer plus drug may have a slower release profile than a polymer soaked in a drug solution. Likewise, a layering technique may provide an even slower release profile than the homogeneous layer of polymer plus drug.

To quantify the release rates, lenses with and without drug can be placed in a known quantity of release media (distilled water or buffered saline) and stirred with a magnetic stirrer. At various times the lenses can be transferred to fresh media and the absorbance of the previous media can be determined by ultraviolet spectroscopy. The absorbance of the media containing drugged lenses is reduced by the absorbance of the media containing undrugged lenses. Use of a calibration curve relating absorbance to concentration allows for a determination of the concentration of the drug. The calibration curve is developed by measuring the absorbance of known concentrations of the drug in the release media. As the concentrations ($\mu$g/ml) of the drug and the volume (ml) of release media are known, the amount of the released drug can be calculated ($\mu$g). This value divided by the time of exposure to the media gives the release rate in $\mu$g/hr which is plotted against time.

For illustration, a sustained-release "sandwich" dosage form prepared with about 12% w/w of pilocarpine hydrochloride in the middle layer would release the drug in distilled water initially at a rate of about 5 $\mu$g/hour and by around 40 hours at a constant rate of about 0.5 $\mu$g/hour. Using the soaking technique for about 24 hours produced a subsequent constant release rate in distilled water of approximately 5 $\mu$g/hour to approximately 20 $\mu$g/hour.

The contact lenses made from the polymer utilized in the instant invention are oxygen permeable. A critical oxygen tension and flux under a lens should be about 10 mm Hg and 2 $\mu$l/(cm$^2$hr.) respectively below which corneal swelling occurs, see Polse and Decker, *Investigative Opththalmology and Visual Science*, 18: 188 (1979). In order to meet these requirements, the lens material must have adequate oxgyen permeability. These more preferred contact lenses have an oxygen permeability of at least about $24 \times 10^{-11}$ cm$^3$cm/(sec.cm$^2$mmHg), are hydrolytically stable, biologically inert and transparent. In comparison, the well-known contact lens polymer polyhydroxyethyl methacrylate has an oxygen permeability value of about one-third of the polymers of this invention.

Additionally, these lenses are hydrolytically stable, meaning that when the contact lenses are placed into an aqueous solution (e.g., on the eye) or during the disinfecting step (i.e., water plus heat), the lenses will not change in chemical composition. That is, they will not hydrolyze. On heating in boiling water for 120 hours, the typical polymer of this invention experiences a water content loss of 3% or less. The most preferred lenses/polymers useful in this invention have a stable water content that undergoes less than 1% change. Thus, the polymers and copolymers disclosed herein can be boiled and/or autoclaved in water without being damaged whereby sterilization may be achieved. In addition sterilization can be achieved by gamma-irradiation, ultraviolet light irradiation and ethylene oxide exposure.

The polymers and copolymers employed in this invention being soft yet resilient and hard to tear are well suited for preparing biomedical devices, including contact lenses, which have the ability to release medications from the polymeric matrix over a prolonged period of time. It is well known that the wearer of soft contact lenses will have an unavoidable amount of handling of the lenses. Part of the cleaning and rinsing procedure is to rub each lens and tearing has been a concern in prior art lenses. The polymers and copolymers used in the present invention have a tear initiation strength (ASTM D-1938) of up to 5 g/mm of thickness.

An article formed from the disclosed polymers and copolymers may be used to administer medications to mammals where an article compatible with living tissue or with the mucous membranes is desired. The term "biomedical devices" means the materials disclosed herein have nontoxic, nonirritating physiochemical properties rendering them suitable for prolonged contact with living tissue, blood and the mucous membranes. It is known that blood, for example, is rapidly damaged in contact with artificial surfaces. The design of a synthetic surface which is antithrombogenic and nonhemolytic to blood is necessary for drug administering devices used with blood, especially an implanted or transdermal device. The polymers and copolymers employed for the purposes of the instant invention are compatible with living tissue.

The instant invention provides a novel sustained-release polymeric hydrogel dosage form useful for topical, systemic or transdermal administration of a medicinal agent comprising the above-described polymeric matrix in association with a therapeutically effective amount of the medicinal agent. The specific polymeric matrix containing an amino acid polymer permits the subsequent release of the active ingredient at a gradual, carefully controlled rate prolonging the time release period. Further, this invention concerns a method of administering a therapeutically effective amount of a medicinal agent over an extended period of time to a mammal in need of the medicinal agent which comprises contacting a tissue of said mammal with the sustained-release polymeric hydrogel dosage form for a sufficient amount of time to achieve a constant therapeutic effect. In contrast to normal disintegration time, the sustained-release administration of medicaments enhances therapeutic effectiveness and decreases many undesirable side effects by maintaining constant tissue and blood levels.

The polymeric hydrogel dosage form can be used in preparing biomedical devices that upon surgical implant will provide sustained-release activity of the active ingredient. Depending on the location of the implant, the therapeutic effect may be local or systemic. The dosage form can also provide for the oral or topical (i.e., localized activity on the skin) controlled-release administration of medicaments. Additionally, the dosage form can be utilized for the transdermal controlled-release administration of medicaments, i.e., the device is retained in contact with the skin for transdermal absorption of the medicament into the blood for systemic effect. Contact with the skin may be achieved by any means well-known in the art such as by incorporating an adhesive in or on the device, adhering the device within or onto a bandage-type article, etc.

Further, the dosage form can be useful for the ophthalmic route of administering medicinal agents for either local or systemic therapeutic effect. The term "ophthalmic administration of a systemic medicament" defines the administration of a medicinal agent to a mammal by the ophthalmic route whereby the medicinal agent acts therapeutically to create a systemic effect. For ophthalmic administration of a medicament to produce local or systemic activity, the polymeric composition can be molded into any convenient shape for eye contact. If correcting vision is not necessary, the dosage form does not have to cover the entire cornea. Alternatively, the polymeric hydrogel can be shaped into contact lenses on optical molds if it is desirable to correct vision in addition to administer ophthalmic medicaments.

The length of time for contacting the polymeric hydrogel device containing a medicament with a tissue of a mammal depends upon the individual circumstances of each case. A sufficient amount of time to achieve a constant therapeutic effect varies in accordance with the optimum therapeutic effect desired. The duration of therapy is, of course, contingent upon the disease or medical problem being treated or palliated. Likewise, the therapeutically effective amount of the specific medicinal agent is determined by therapy requirements and the biophysical properties of the active compound. For example, with respect to contact lenses, the invention contemplates daily wear or extended wear, typically, up to a month. To treat an eye infection, it would be desirable to maintain the contact lens containing an antibiotic or an antiviral agent on the eye for one to two weeks. On the other hand, to treat glaucoma, it would be desirable to wear the lens containing an agent for reducing intraocular pressure for the maximum time that extended wear contact lenses can remain in the eye.

The term "dosage form" refers to physically discrete units suitable as unitary dosage for mammals, each unit containing a predetermined quantity of active component calculated to produce the desired therapeutic effect. The novel sustained-release dosage form of this invention is indicated by the physical or chemical characteristics of the active component and the particular therapeutic effect to be achieved.

The term "a medicinal agent" means a substance used in treating or ameliorating a disease or medical condition. For purposes of this invention, "a medicinal agent" refers to drugs which would have the capacity to be bound to the amino acid moiety of the polymeric hydrogel. That is, any drug or its salt with polar characteristics that interacts with amino acids in a favorable way could be used in the present invention. Examples of medicinal agents include, but are not limited to, antibiotics, antivirals, anti-inflammatories, steroids, peptides, polypeptides, cardiotonics, antihypertensives, antiallergics, alpha- and beta-adrenergic blocking agents, anticataract agents, ophthalmic medicaments, opthalmic lubricating agents, ophthalmic topical or regional anesthetic agents, etc. The ophthalmic medicaments or other medicinal agents encompass such drugs as pilocarpine, idoxuridine, carbachol, bethanechol, timolol, tetracycline, epinephrine, phenylephrine, eserine, phospholine, demecarium, cyclopentolate, homatropine, scopolamine, nitroglycerin, chlortetracycline, bacitracin, neomycin, polymyxin, gramicidin, oxytetracycline, chloramphenicol, gentamycin, penicillin, erythromycin, sulfacetamide, polymyxin B, tobramycin, isofluorophate, fluoromethalone, dexamethasone, hydrocortisone, fluorocinolone, medrysone, prednisolone, methyl prednisolone, betamethasone, triamcinolone, interferon, cromolyn, all-trans-retinoic acid (Vitamin A), the nontoxic, pharmaceutically acceptable salts thereof and the like. The category of ophthalmic lubricating agents refers to those agents capable of inducing natural lacrimation or creating artificial lacrimation and includes, for example, polyvinyl alcohol, cellulose polymers such as hydroxypropyl methyl cellulose, a polylactam such as polyvinyl pyrrolidinone and other tear inducers or substitutes. The topical or regional anesthetic agents, which may be useful during ophthalmic surgery or other ophthalmic procedures, include lidocaine, cocaine, benoxinate, dibucaine, proparacaine, tetracaine, etidocaine, procaine, hexylcaine, bupivacaine, mepivacaine, prilocaine, chloroprocaine, etc.

The term "pharmaceutically acceptable salt" refers to those salts of the parent compound which do not significantly or adversely affect the pharmaceutical properties (e.g., toxicity, efficacy, etc.) of the parent compound. The salts of the present invention which are pharmaceutically acceptable include for example, chloride, iodide, bromide, hydrochloride, acetate, nitrate, stearate, phosphate, sulfate etc. It is desirable to use the appropriate salt form of the active ingredient which would increase the water solubility or polar characteristics of the base compound.

The following examples demonstrate certain aspects of the present invention. However, it is to be understood that these examples are for illustrative purposes only and do not purport to be wholly definitive as to conditions and scope of this invention. All parts and percents referred to herein are on a weight basis and all temperatures are expressed in degrees Celsius unless otherwise specified. It also should be appreciated that when typical reaction conditions (e.g., temperature, reaction times) have been given, the conditions which are both above and below these specified ranges can also be used, though generally less conveniently.

A further understanding of the invention may be obtained from the following nonlimiting examples. These examples were conducted at room temperature (about 23° C. to about 28° C.) and at atmospheric pressure.

EXAMPLE 1

Preparation of Hydrogel Polymer

A clear, homogeneous solution is prepared by mixing together 83.5 g of 2-hydroxyethyl methacrylate (HEMA), 10 g of isobornyl methacrylate (IBOMA), 6 g of methacroyl glycine (MG) and 0.5 g of ethylene glycol dimethacrylate (EGDMA). To the mixture is added 0.5 g of benzoin methyl ether (BME). The clear solution of monomers (A) is polymerized under hot ultraviolet light (UV) for 15 minutes against a suitable optical mold under an inert atmosphere. Water content is about 60%.

EXAMPLE 2

Soaking Method

The procedure of Example 1 is repeated to prepare the hydrogel polymer. The polymer is soaked in an aqueous solution of 4% w/w pilocarpine hydrochloride for 24 hours.

EXAMPLE 3

Preparation of Single-Layer Hydrogel Polymer Containing Medicament

Solution A is prepared in accordance with the procedure of Example 1. To the solution is added 11.43 g of pilocarpine hydrochloride. The clear, homogeneous solution (B) is placed on a suitable spincasting optical mold. It is spin cast under UV and nitrogen for 40 minutes.

EXAMPLE 4

Preparation of Triple-Layer Hydrogel Polymer Containing Medicament

Solutions A and B are prepared in accordance with the respective procedures of Examples 1 and 3. On a suitable spincasting optical mold is injected 9.8 µl of solution A and is spin cast under UV and nitrogen for 5 minutes at 300 rpm. On the resulting polymer is injected 29.4 µl of solution B. Spin casting is repeated in the same manner as for the first layer. On the second polymer layer is injected 9.8 µl of solution A. The same spin casting technique is again repeated. The result is a triple-spun contact lens with a polymer-drug layer encapsulated between two polymer layers without the drug.

EXAMPLE 5

Release Studies I

Figure 8:
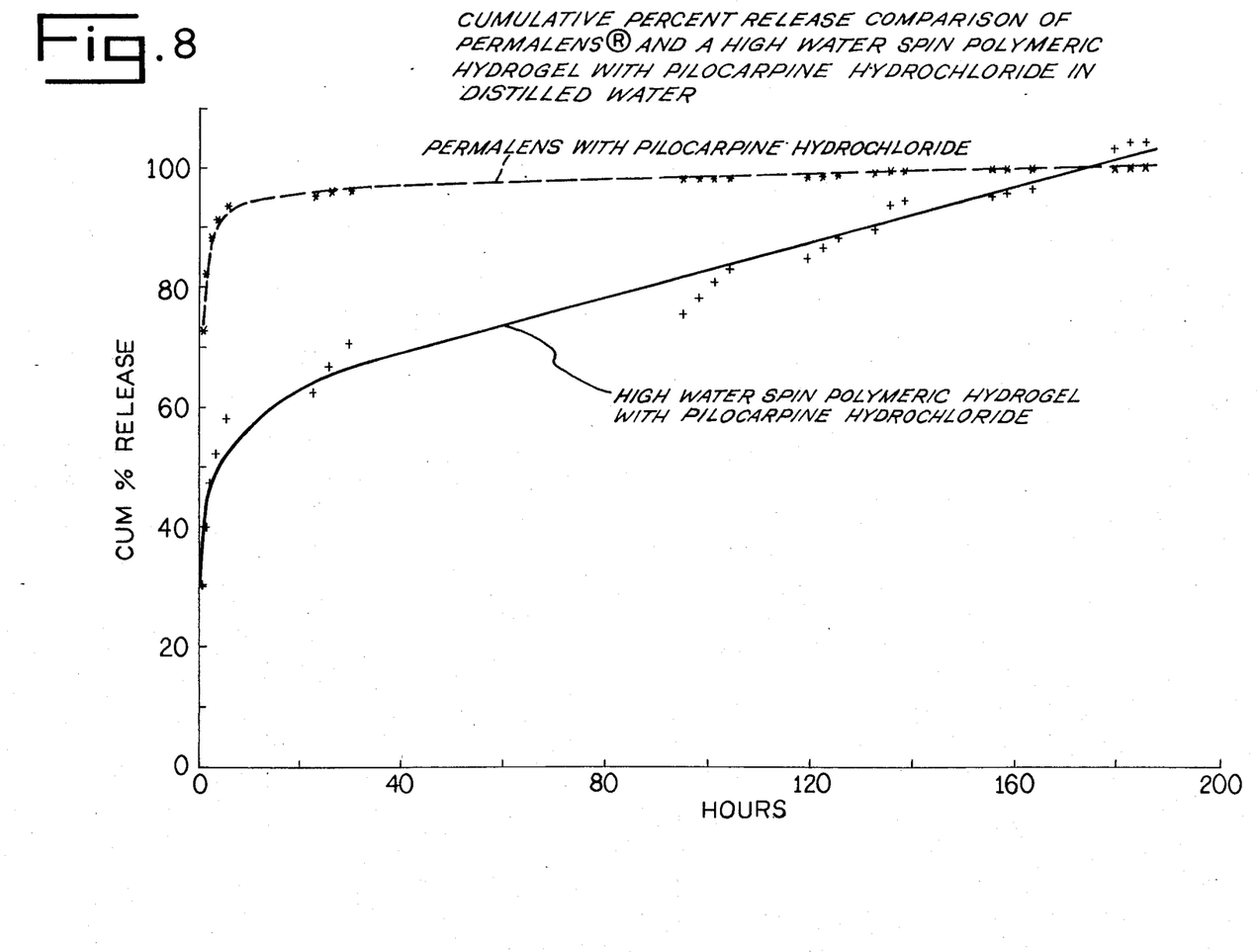
FIG. 8 is a cumulative percent release comparison of Permalens ® and a high water spin polymeric hydrogel with pilocarpine hydrochloride in distilled water.
Figure 9:
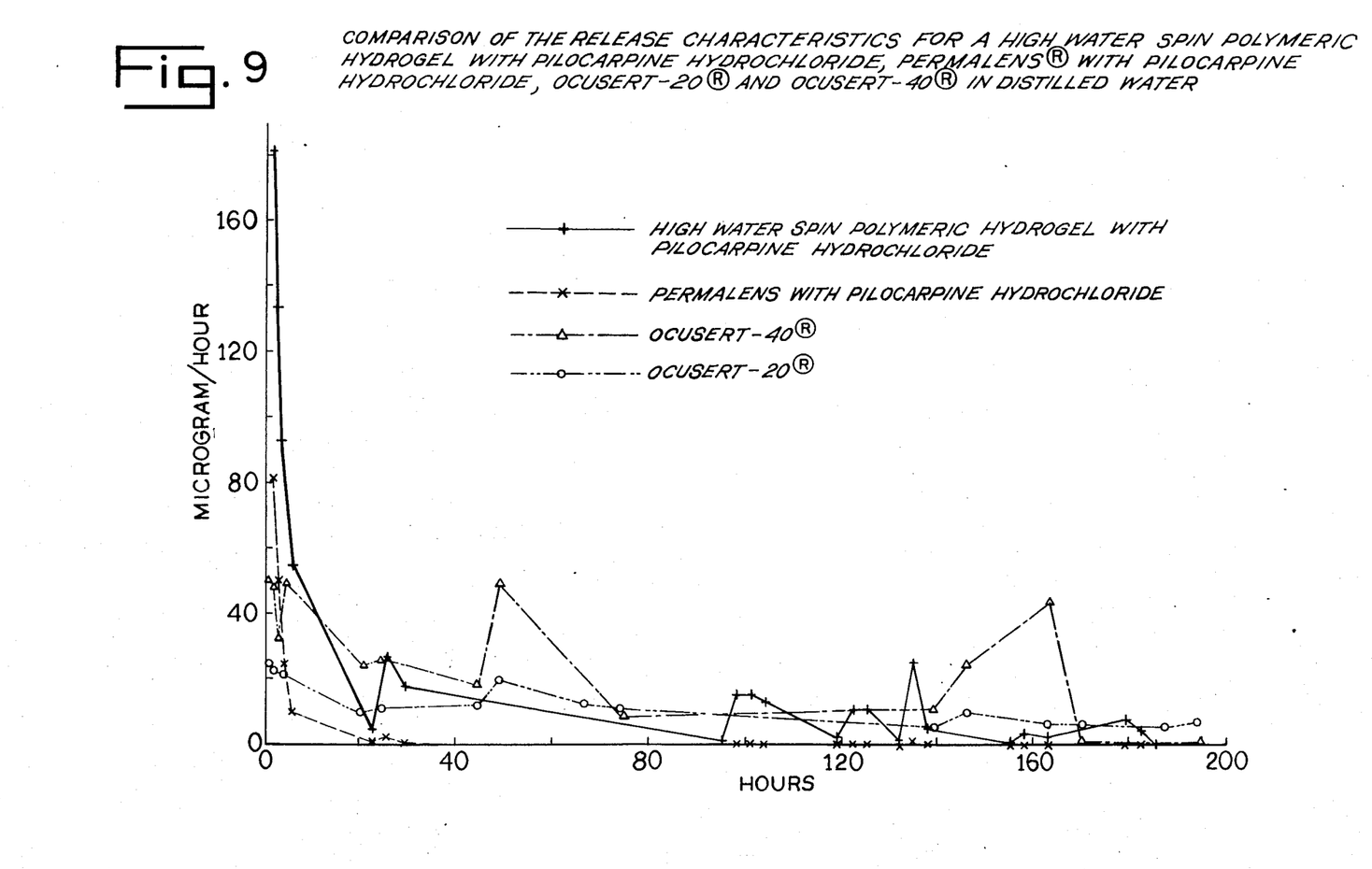
FIG. 9 is a comparison of the release characteristics for a high water spin polymeric hydrogel with pilocarpine hydrochloride, Permalens ® with pilocarpine hydrochloride, Ocusert-20 ® and Ocusert-40 ® in distilled water.
Figure 10:
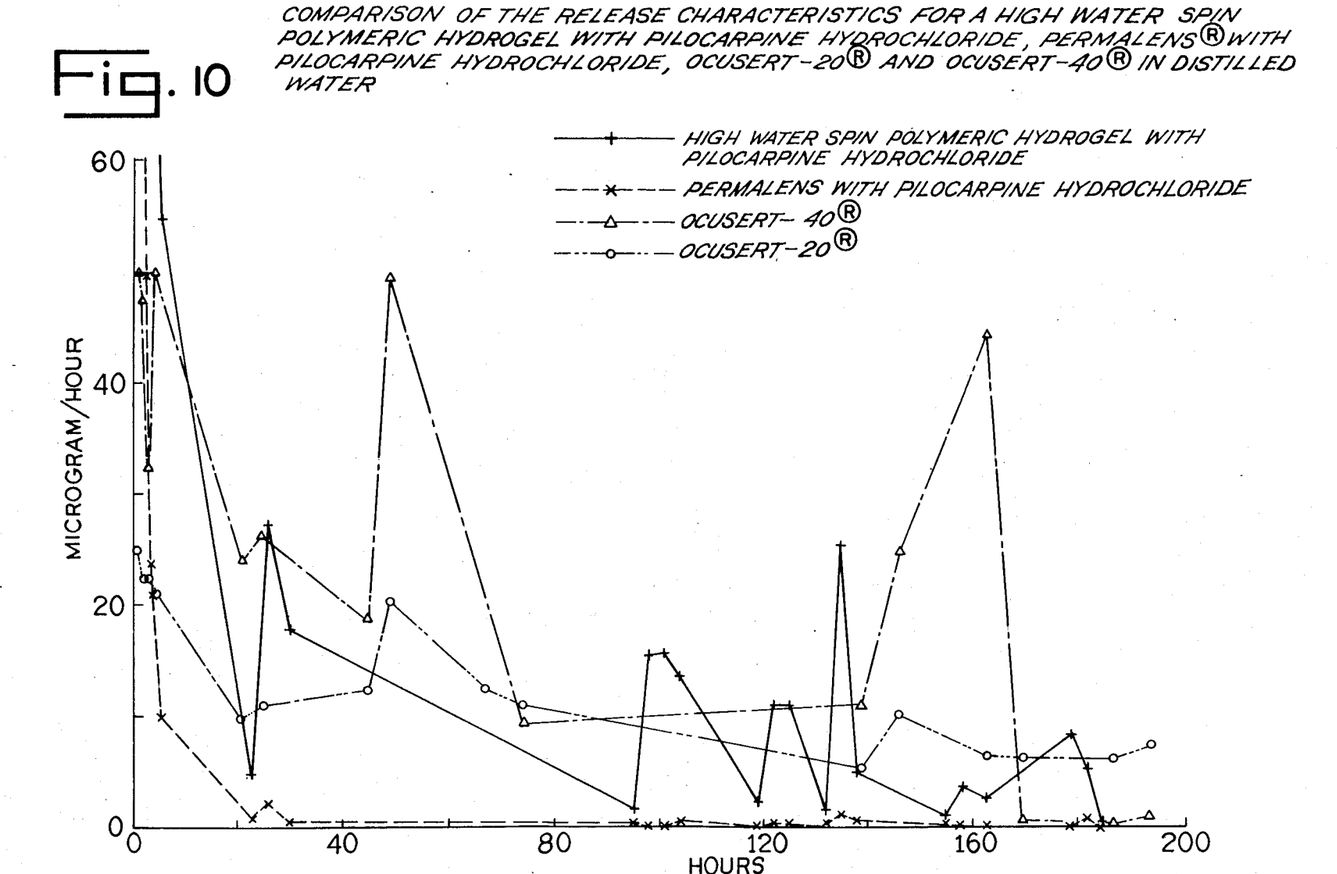
FIG. 10 is the same comparison as FIG. 9 on an expanded scale.
Figure 13:
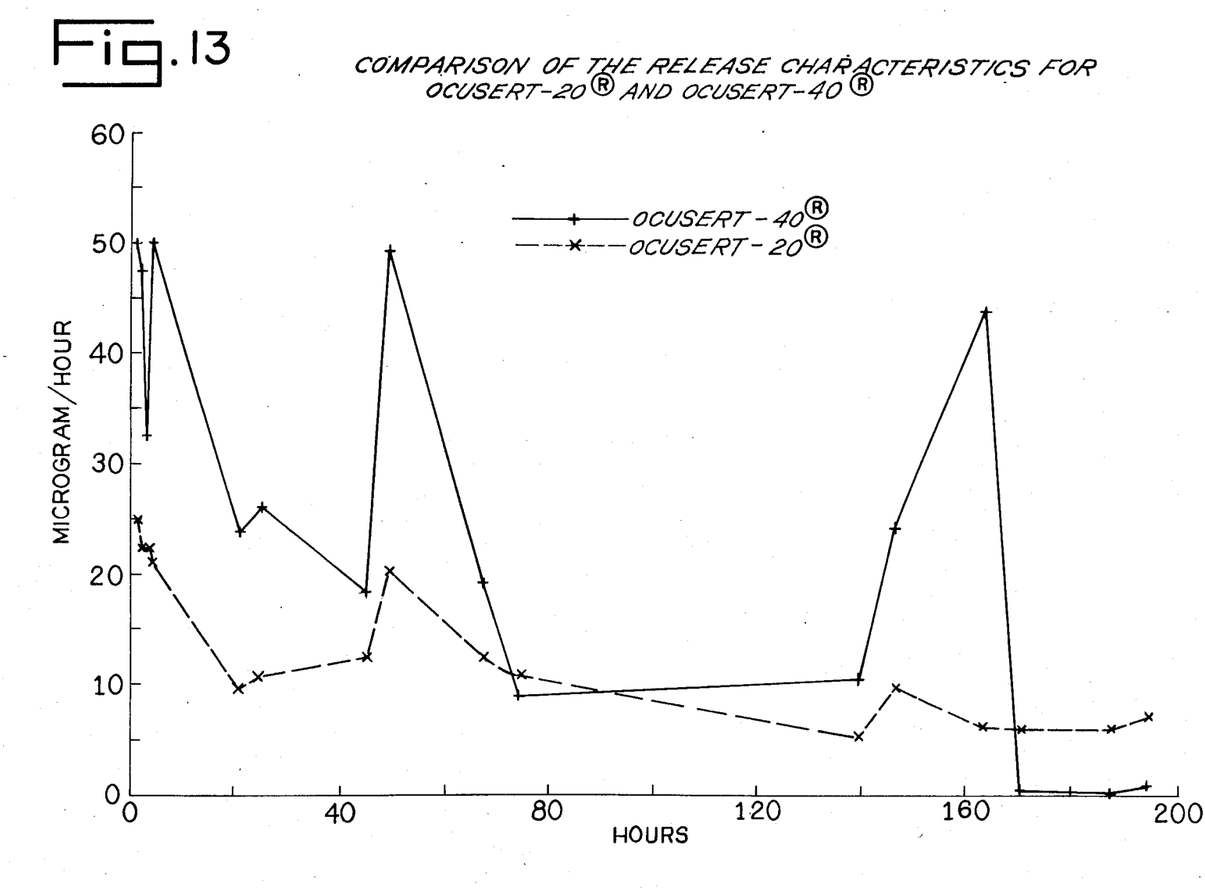
FIG. 13 is a comparison of the release characteristics for Ocusert-20 ® and Ocusert-40 ®.

The procedure of Example 1 is repeated to prepare the hydrogel polymer. The polymer, Ocusert-20 ®, Ocusert-40 ® and Permalens ® are separately soaked in an aqueous solution of 4% w/w pilocarpine hydrochloride for 17 hours. Each lens is then separately placed in distilled water with stirring. With appropriate controls, the release rate of the drug into the water is measured. The results are shown in FIGS. 1-4 illustrating the release characteristics of the hydrogel polymer used in this invention, Ocusert-20 ®, Ocusert-40 ® and Permalens ®, respectively. A percent release comparison of the Permalens ® and the hydrogel polymer is set forth in FIG. 8. The raw data release characteristics obtained by this experiment are supplied in FIGS. 9, 10 and 13.

EXAMPLE 6

Release Studies II

Figure 1:
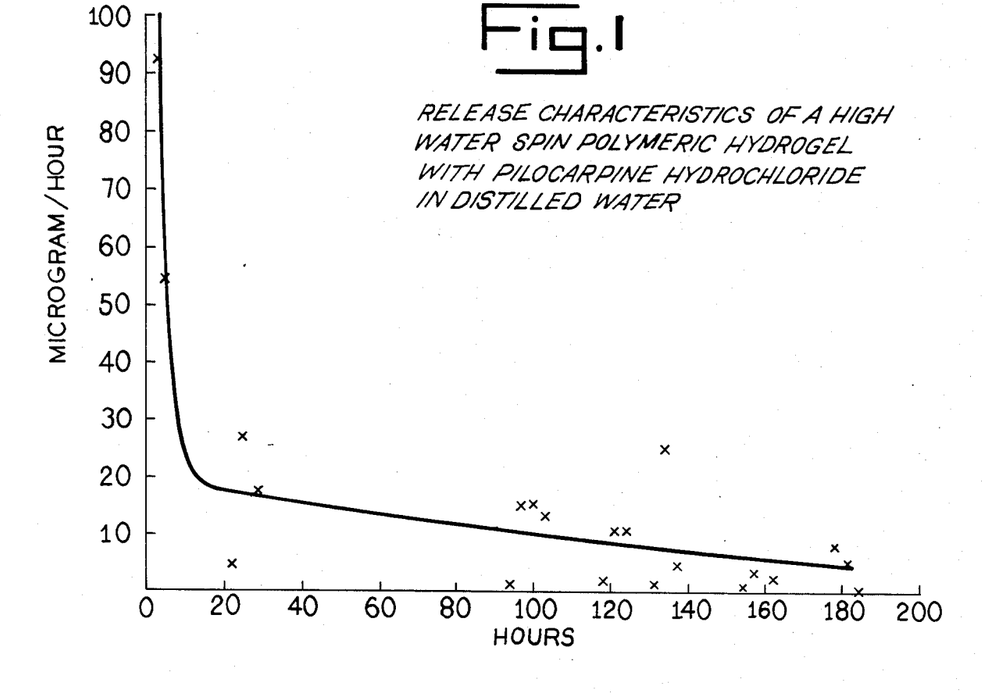
FIG. 1 is the release characteristics of a high water spin polymeric hydrogel with pilocarpine hydrochloride in distilled water.
Figure 2:
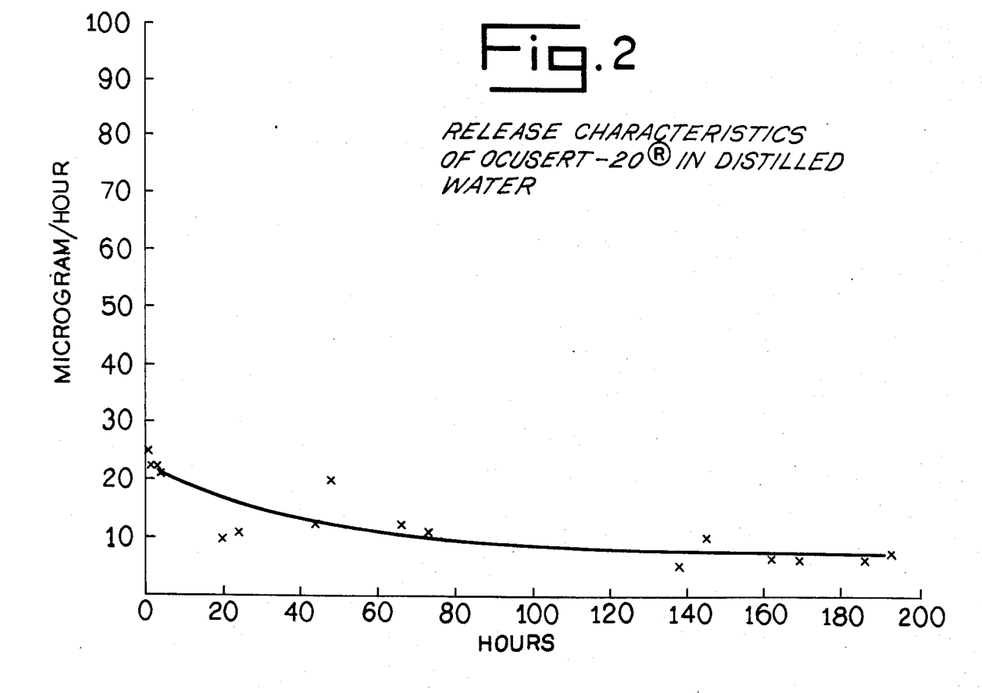
FIG. 2 is the release characteristics of Ocusert-20 ® (an ophthalmic sustained-release device using an ethylenevinyl acetate copolymer as the rate controlling membrane with pilocarpine, available from Alza Corp., Palo Alto, Calif.) in distilled water.
Figure 3:
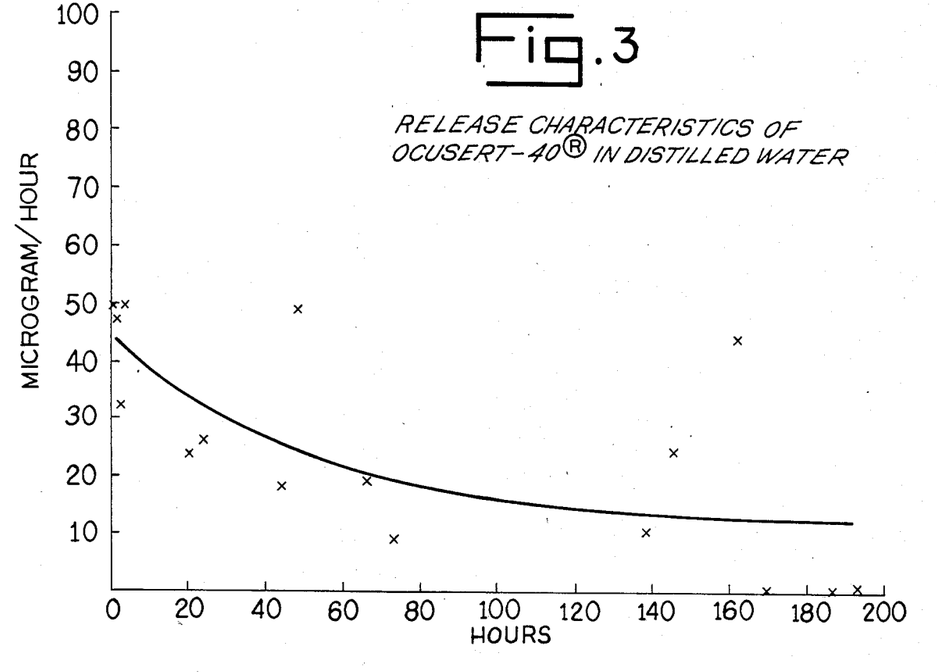
FIG. 3 is the release characteristics of Ocusert-40 ® (an ophthalmic sustained-release device using an ethylenevinyl acetate copolymer as the rate controlling membrane with pilocarpine, available from Alza Corp., Palo Alto, Calif.) in distilled water.
Figure 4:
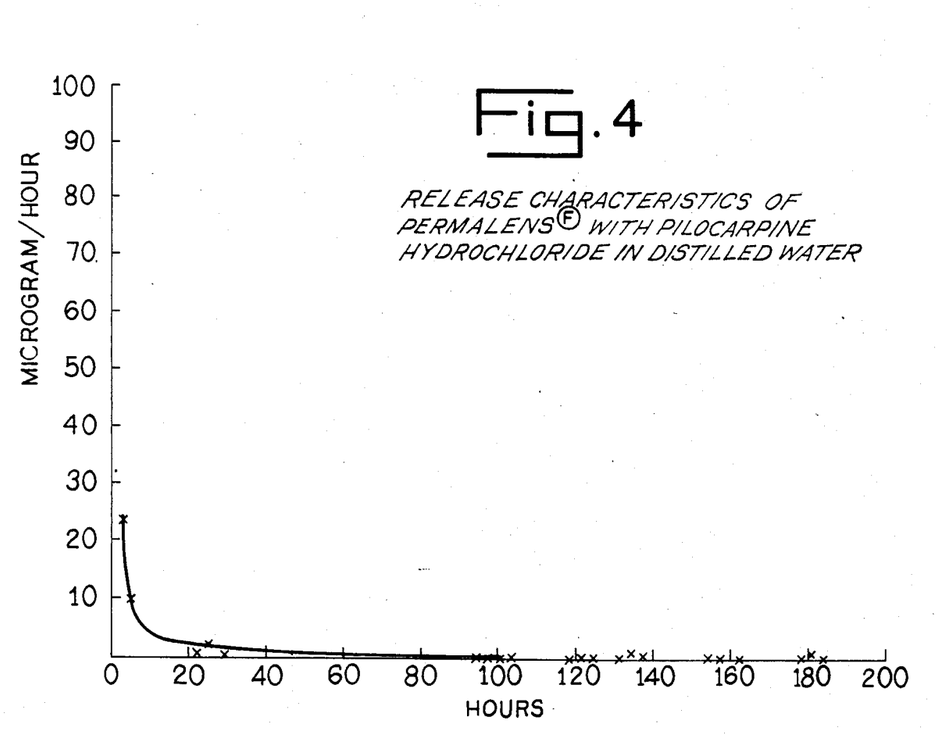
FIG. 4 is the release characteristics of Permalens ® (an extended wear contact lens comprising hydroxyethyl methacrylate vinyl pyrrolidone with methacrylic acid, available from Cooper Vision Incorp., Mountain View, Calif.) with pilocarpine hydrochloride in distilled water.
Figure 5:
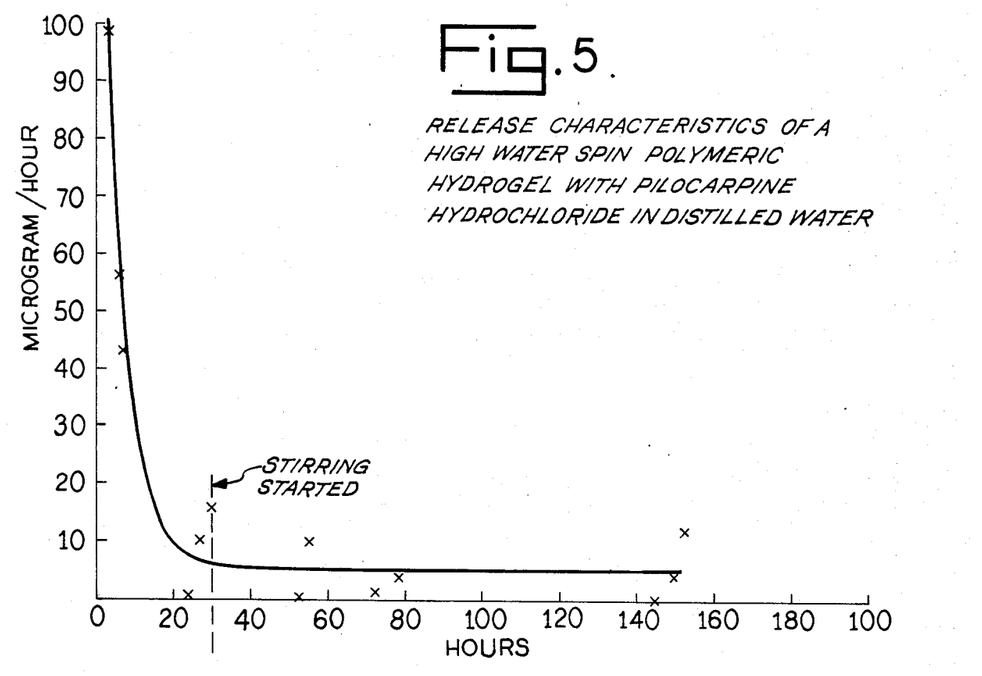
FIG. 5 is the release characteristics of a high water spin polymeric hydrogel with pilocarpine hydrochloride in distilled water.
Figure 6:
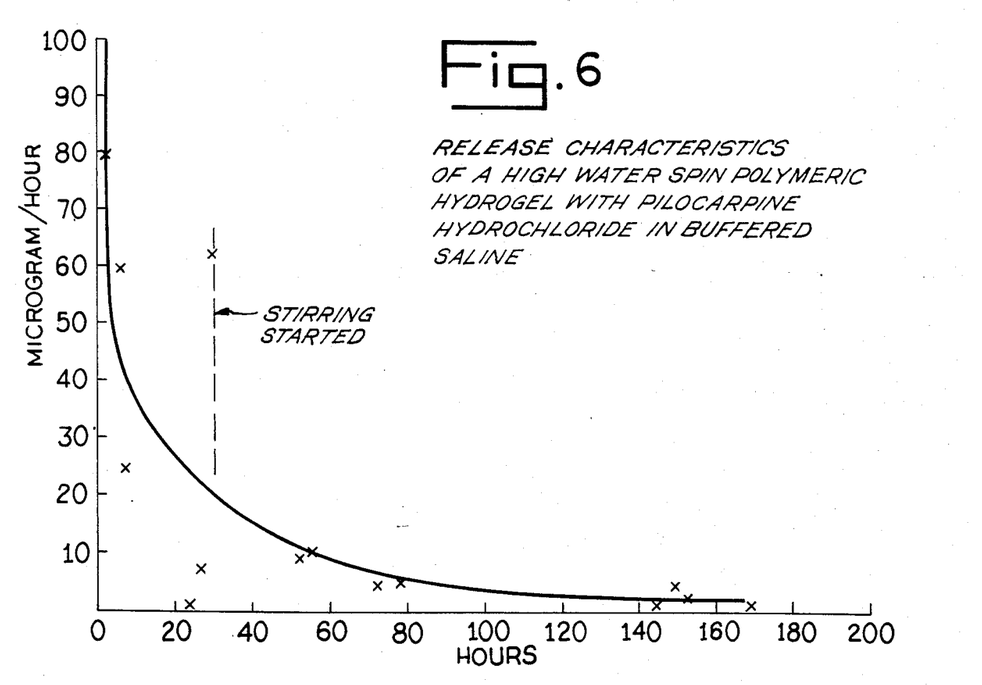
FIG. 6 is the release characteristics of a high water spin polymeric hydrogel with pilocarpine hydrochloride in buffered saline.
Figure 11:
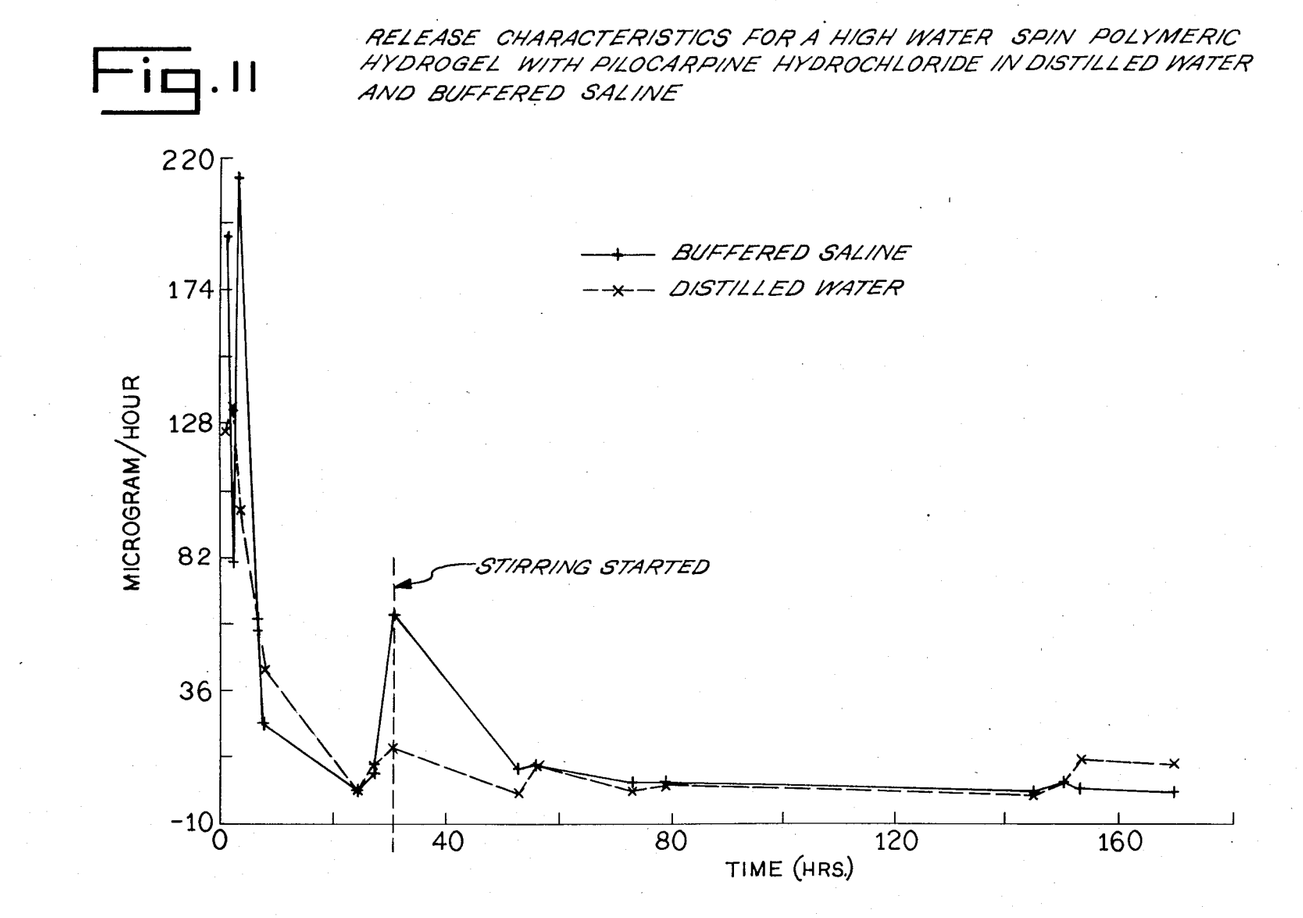
FIG. 11 is a comparison of the release characteristics for a high water spin polymeric hydrogel with pilocarpine hydrochloride in distilled water and buffered saline.
Figure 12:
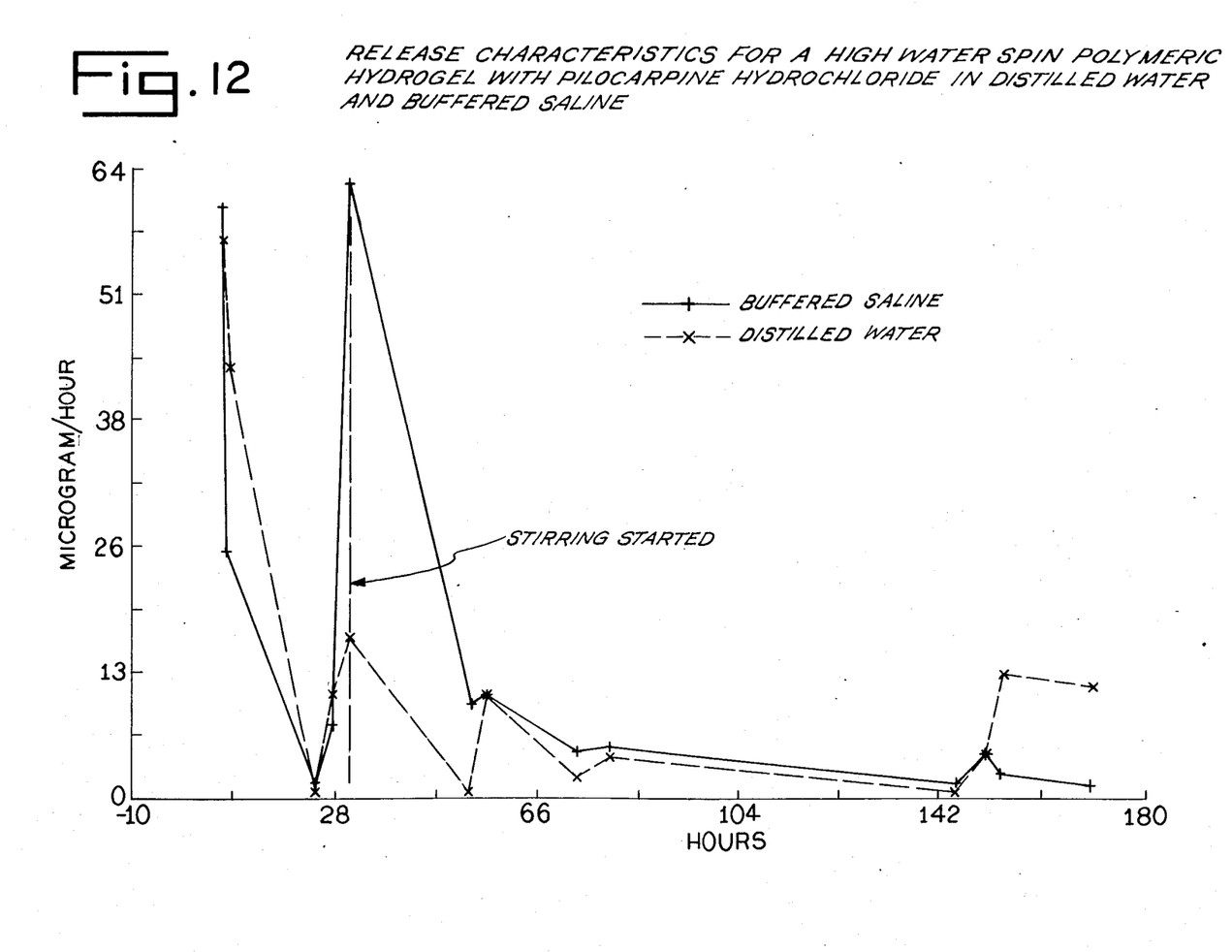
FIG. 12 is the same comparison as FIG. 11 on an expanded scale.

The procedure of Example 1 is repeated to prepare two hydrogel polymers. The two polymers and two Soflens ® lenses (polymacon soft contact lens available from Bausch & Lomb) are separately soaked in an aqueous solution of 4% w/w pilocarpine hydrochloride for 17 hours. One of each type of lens is placed in buffered saline and distilled water respectively. The Soflens ® released all the drug present in 1½ hours and 2½ hours in the buffered saline and distilled water respectively. The release characteristics of the polymers are illustrated in FIGS. 5 and 6 for the respective distilled water and buffered saline tests. The raw data release characteristics are illustrated in FIGS. 11 and 12.

EXAMPLE 7

Release Studies III

Figure 7:
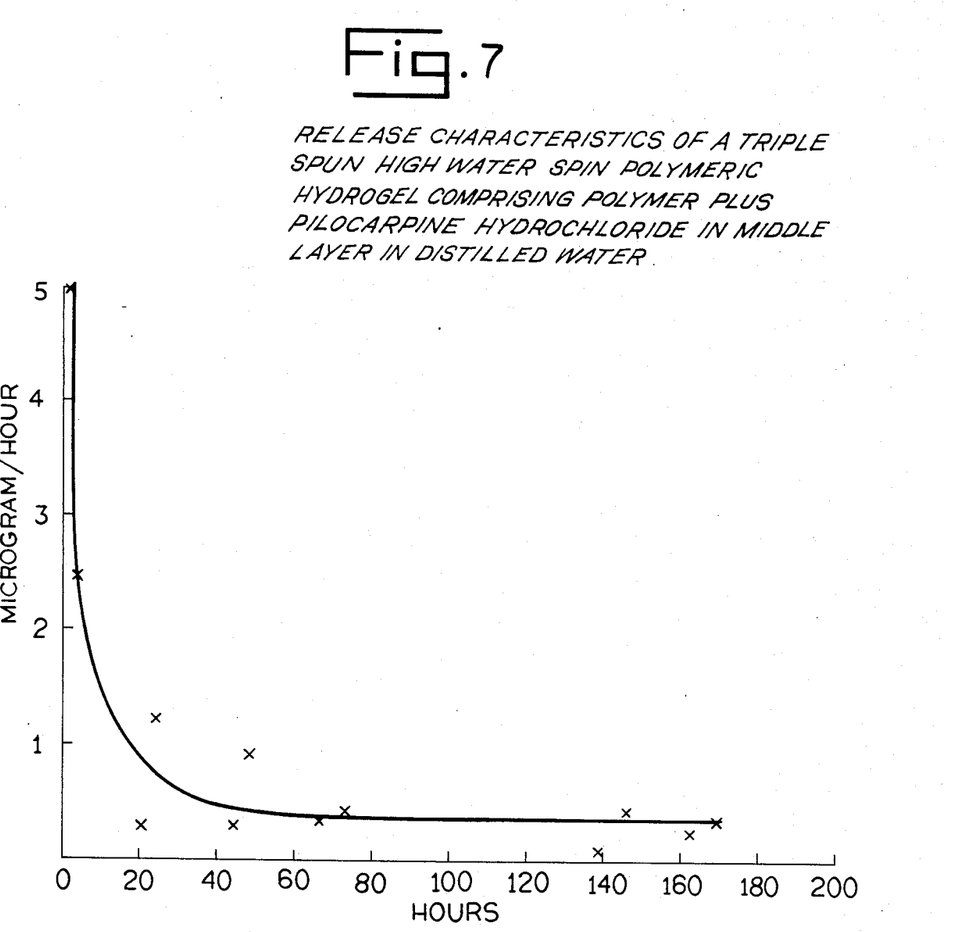
FIG. 7 is the release characteristics of a triple spun high water spin polymeric hydrogel comprising polymer plus pilocarpine hydrochloride in middle layer in distilled water.

The procedure of Example 4 is repeated to prepare a triple-layer hydrogel polymer containing pilocarpine hydrochloride. The polymer is placed in distilled water and the release rate is measured. The results are shown in FIG. 7 illustrating the release characteristics of the product of Example 4.

In the foregoing there has been provided a detailed description of preferred embodiments of the present invention for the purpose of illustration and not limitation. It is to be understood that all other modifications, ramifications and equivalents obvious to those having skill in the art based on this disclosure are intended to be within the scope of the invention as claimed.

What is claimed is:

1. A sustained-release polymeric hydrogel dosage form useful for topical, systemic or transdermal administration of a medicinal agent comprising a cross-linked, polymerized hydrophilic polymer including an amino acid moiety in the polymer, and said medicinal agent in a therapeutically effective amount.

2. The sustained-release dosage form of claim 1 wherein the polymer includes therein a hydrophobic component.

3. The sustained-release dosage form of claim 1 or 2 wherein the amino acid moiety is derived from an aliphatic monocarboxylic acid, an aliphatic dicarboxylic acid, an aromatic dicarboxylic acid, an aromatic tricarboxylic acid or an aromatic tetracarboxylic acid.

4. The sustained-release dosage form of claim 1 or 2 wherein the amino acid moiety is derived from methacroyl glycine, methacroyl glutamate, methacroyl desmosine or methacroyl isodesmosine.

5. The sustained-release dosage form of claim 1 or 2 wherein said medicinal agent is an antibiotic, an antiviral, an anti-inflammatory, a steroid, a peptide, a polypeptide, a cardiotonic, an antihypertensive, an antiallergic, an alpha-adrenergic blocking agent, a beta-adrenergic blocking agent, an anticataract agent, an ophthalmic medicament, an ophthalmic lubricating agent or an ophthalmic anesthetic agent.

6. The sustained-release dosage form of claim 1 or 2 wherein said medicinal agent is selected from the group consisting of pilocarpine, idoxuridine, carbachol, bethanechol, timolol, tetracycline, epinephrine, phenylephrine, eserine, phospholine, demecarium, cyclopentolate, homatropine, scopolamine, nitroglycerin, chlortetracycline, bacitracin, neomycin, polymyxin, gramicidin, oxytetracycline, chloramphenicol, gentamycin, penicillin, erythromycin, sulfacetamide, polymyxin B, tobramycin, isofluorophate, fluoromethalone, dexamethasone, hydrocortisone, fluorocinolone, medrysone, prednisolone, methyl prednisolone, betamethasone, triamicinolone, interferon, cromolyn, all trans-retinoic acid and a nontoxic, pharmaceutically acceptable salt thereof.

7. The sustained-release dosage form of claim 1 or 2 wherein said medicinal agent is an ophthalmic lubricating agent selected from the group consisting of polyvinyl alcohol, a cellulose polymer and a polylactam.

8. The sustained-release dosage form of claim 1 or 2 wherein said medicinal agent is an ophthalmic anesthetic agent.

9. The sustained-release dosage form of claim 1 or 2 wherein said dosage form is molded as a contact lens or ocular insert for ophthalmic administration of a systemic medicament, an ophthalmic medicament or an ophthalmic lubricating agent.

10. The sustained-release dosage form of claim 1 or 2 wherein said dosage form is molded as a contact lens for ophthalmic administration of a systemic medicament, an ophthalmic medicament or an ophthalmic lubricating agent and retains the ability to correct vision.

11. The sustained-release dosage form of claim 2 wherein a polymeric hydrogel is prepared from a polymerizable hydrophilic monomer present in the amount of about 50% to about 90% w/w, an amino acid monomer present in the amount of about 5% to about 27% w/w, a cross-linking agent present in the amount of about 0.1% to about 20% w/w and a hydrophobic monomer present in the amount of about 8% to about 20% w/w, the weight percent being based on the total weight of the polymeric hydrogel.

12. A method of administering a therapeutically effective amount of a medicinal agent over an extended period of time to a mammal in need of the medicinal agent for local or systemic effect which comprises contacting a tissue of said mammal with the sustained-release dosage form of claim 1 or 2 for a prolonged period of time.

13. A method of administering a therapeutically effective amount of an ophthalmic medicament over an extended period of time to a mammal in need of the medicament which comprises contacting an eye tissue of said mammal with the sustained-release dosage form of claim 1 or 2 for a prolonged period of time, wherein said medicinal agent is the ophthalmic medicament.

14. A method of administering a therapeutically effective amount of an ophthalmic lubricating agent over an extended period of time to a mammal in need of the agent which comprises contacting an eye tissue of said mammal with the sustained-release dosage form of claim 1 or 2 for a prolonged period of time, wherein said medicinal agent is the ophthalmic lubricating agent.

15. A method of administering a therapeutically effective amount of an ophthalmic anesthetic agent over an extended period of time to a mammal in need of ophthalmic anesthesia which comprises contacting an eye tissue of said mammal with the sustained-release dosage form of claim 1 or 2 for a prolonged period of time, wherein said medicinal agent is the ophthalmic anesthetic agent.

16. A method of treating glaucoma in a mammal suffering from glaucoma which comprises contacting an eye tissue of said mammal with the sustained-release dosage form of claim 1 or 2, wherein said medicinal agent is an agent for reducing intraocular pressure for a prolonged period of time.

17. A method of treating glaucoma in a mammal suffering from glaucoma which comprises contacting an eye tissue of said mammal with the sustained-release dosage form of claim 1 or 2, wherein said medicinal agent is timolol, pilocarpine or a nontoxic, pharmaceutically acceptable salt thereof for a prolonged period of time.

18. A method of inducing natural lacrimation or creating artificial lacrimation in a mammal suffering from deficient lacrimation which comprises contacting an eye tissue of said mammal with the sustained-release dosage form of claim 1 or 2 for a prolonged period of time, wherein said medicinal agent is an ophthalmic lubricating agent.

19. A process for the preparation of the sustained-release dosage form of claim 1 which comprises preparing a homogeneous solution or suspension by mixing a hydrophilic monomer, an amino acid monomer, a cross-linking agent and a medicinal agent and polymerizing the solution or suspension.

20. A process for the preparation of the sustained-release dosage form of claim 1 which comprises preparing a homogeneous solution A by mixing a hydrophilic monomer, an amino acid monomer and a cross-linking agent; preparing a homogeneous solution or suspension B by mixing the hydrophilic monomer, the amino acid monomer, the cross-linking agent and a medicinal agent; polymerizing a portion of solution A; polymerizing solution or suspension B on top of polymerized solution A; and polymerizing remainder of solution A on top of polymerized solution or suspension B.

21. A process for the preparation of the sustained-release dosage form of claim 1 which comprises preparing a homogeneous solution by mixing a hydrophilic monomer, an amino acid monomer and a cross-linking agent, polymerizing the solution into a polymer and soaking the polymer in an aqueous solution or suspension of a therapeutically effective amount of a medicinal agent for a sufficient amount of time for equilibration.

22. A process for the preparation of the sustained-release dosage form of claim 2 which comprises preparing a homogeneous solution or suspension by mixing a hydrophilic monomer, an amino acid monomer, a cross-linking agent, a hydrophobic monomer and a medicinal agent and polymerizing the solution or suspension.

23. A process for the preparation of the sustained-release dosage form of claim 2 which comprises preparing a homogeneous solution A by mixing a hydrophilic monomer, an amino acid monomer, a cross-linking agent and a hydrophobic monomer; preparing a homogeneous solution or suspension B by mixing the hydrophilic monomer, the amino acid monomer, the cross-linking agent, the hydrophobic monomer and a medicinal agent; polymerizing a portion of solution A; polymerizing solution or suspension B on top of polymerized solution A; and polymerizing remainder of solution A on top of polymerized solution or suspension B.

24. A process for the preparation of the sustained-release dosage form of claim 2 which comprises preparing a homogeneous solution by mixing a hydrophilic monomer, an amino acid monomer, a cross-linking agent and a hydrophobic monomer, polymerizing the solution into a polymer and soaking the polymer in an aqueous solution or suspension of a therapeutically effective amount of a medicinal agent for a sufficient amount of time for equilibration.

25. The process of claim 19, 20, 21, 22, 23 or 24 wherein a catalyst is used.

26. The process of claim 19, 20, 21, 22, 23 or 24 wherein a catalyst and a mold are used.

27. The process of claim 19, 20, 21, 22, 23 or 24 wherein a catalyst is used and the polymerizing step involves spin casting.

* * * * *